United States Patent [19]
Chen

[11] Patent Number: 5,457,503
[45] Date of Patent: Oct. 10, 1995

[54] SPECTACLES WITH HIGH EFFICIENT ANGLE ADJUSTMENT

[76] Inventor: Jimmy Chen, 3F, No. 92, Ning-Po-Hsi St., Taipei, Taiwan

[21] Appl. No.: 352,347

[22] Filed: Dec. 8, 1994

[51] Int. Cl.⁶ ..................................... G02C 1/04
[52] U.S. Cl. ..................... 351/105; 351/106; 351/120
[58] Field of Search ..................... 351/105, 106, 351/107, 108, 109, 111, 115, 121, 47, 57, 59, 103, 104, 41, 120, 83, 86; 2/450, 451, 452

[56] References Cited

U.S. PATENT DOCUMENTS

5,357,292  10/1984  Wiedner ............................ 351/115

*Primary Examiner*—William L. Sikes
*Assistant Examiner*—Hung Xuan Dang
*Attorney, Agent, or Firm*—Christensen, O'Connor, Johnson & Kindness

[57] ABSTRACT

The pair of spectacles includes an eye-protecting piece with a transparent plate and two side plates, and a U-shaped frame member. Each of the side plates has an upper section with a top edge, an elongated notch extending downwardly from the top edge, and a plurality of parallel ridges projecting from an inner surface and defining a plurality of parallel grooves which extend between the notch and a free end portion thereof. The frame member has an elongated intermediate portion with two side portions. Each of the side portions has an inner surface formed with a hollow rectangular sleeve constituted by a first wall portion which extends perpendicularly from the side portion, a second wall portion spaced farther away from the intermediate portion than the first wall portion and extending perpendicularly from the side portion, and a third wall portion interconnecting the first and second wall portions. The third wall portion has a resilient projection extending toward the side portion. After assembly, a portion of the side plate between the notch and the free end portion thereof extends into the sleeve such that the first wall portion is received slidably in the notch, the second wall portion engages the free end portion of the side plate while the resilient projection engages one of the grooves.

3 Claims, 6 Drawing Sheets

SPECTACLES WITH HIGH EFFICIENT ANGLE ADJUSTMENT

BACKGROUND OF THE INVENTION

1. Field of the Invention

The invention relates to a pair of spectacles, more particularly to a pair of spectacles with an eye-protecting piece that can be connected easily and securely to a frame member and that can be adjusted angularly relative to the frame member.

2. Description of the Related Art

Figure 1:
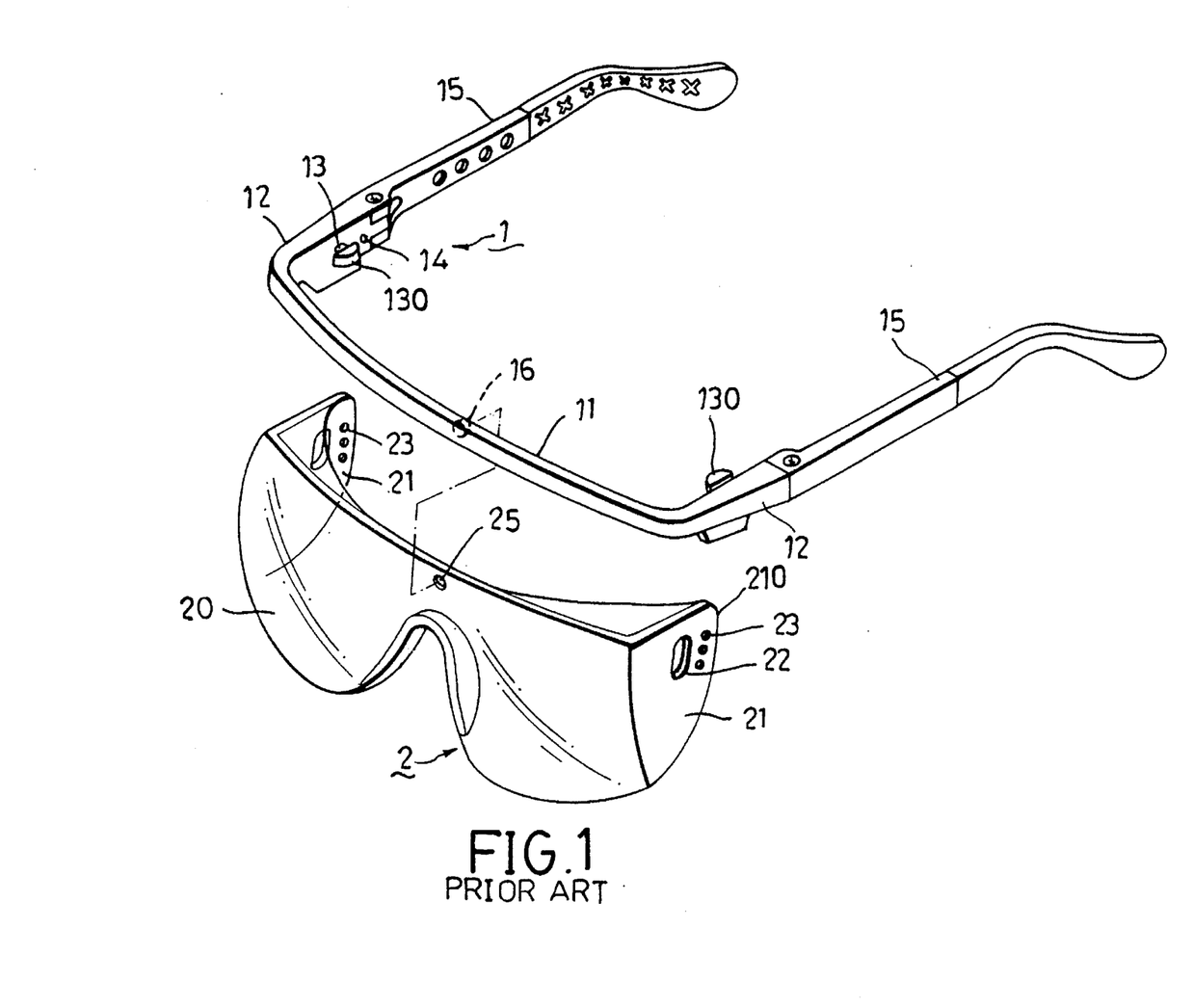
FIG. 1 shows an exploded view of a pair of conventional spectacles.

Referring to FIG. 1, a pair of conventional spectacles is shown to comprise an eye-protecting piece 2 to be disposed in front of the user's eyes and a U-shaped frame member 1 to be provided around an upper edge portion of the eye-protecting piece 2.

The eye-protecting piece 2 includes an elongated transparent plate 20 with two opposed ends and an upper edge portion which is formed with a through-hole 25 between the opposed ends, and a pair of side plates 21 which extend symmetrically from the opposed ends of the transparent plate 20, thereby forming two free end portions 210. Each of the side plates 21 has an upper section with a top edge, a slot 22 formed through the upper section and extending toward a lower section of the side plates 21, and a row of dents 23 formed on an outer surface of the upper section and located between the slot 22 and a corresponding one of the free end portions 210. Note that the dents 23 are staggered with one another.

The U-shaped frame member 1 has an elongated intermediate portion 11 with a protuberance 16 and two side portions 12 which extend from two opposed ends of the intermediate portion 11. Each of the two side portions 12 has an engaging lug 13 with an enlarged head 130 and a boss 14 adjacent to the engaging lug 13. A pair of legs 15 are mounted pivotally and respectively to the free ends of the side portions 12.

Figure 2:
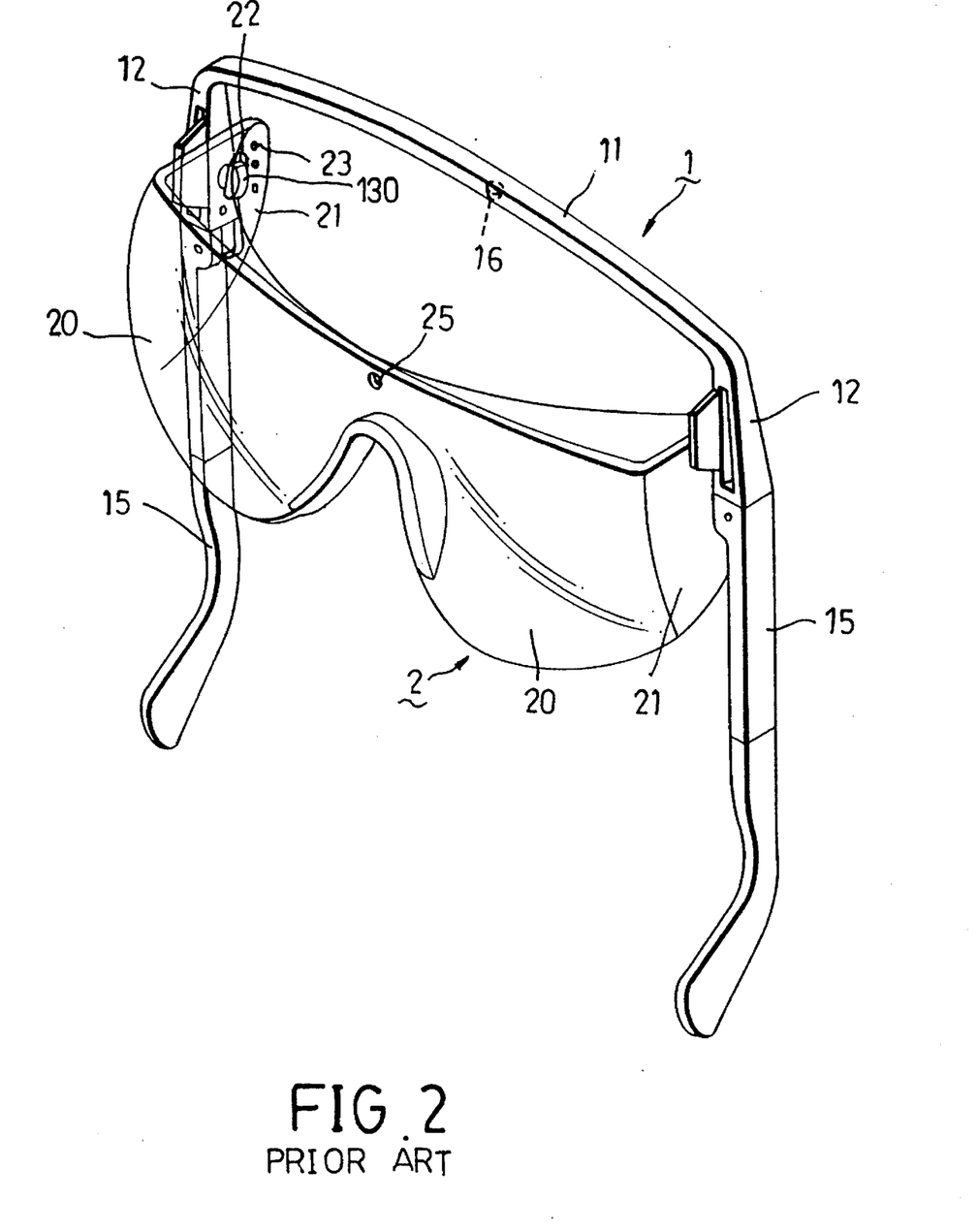
FIG. 2 illustrates how an eye-protecting piece and a frame member are connected to form the conventional spectacles shown FIG. 1.
Figure 3:
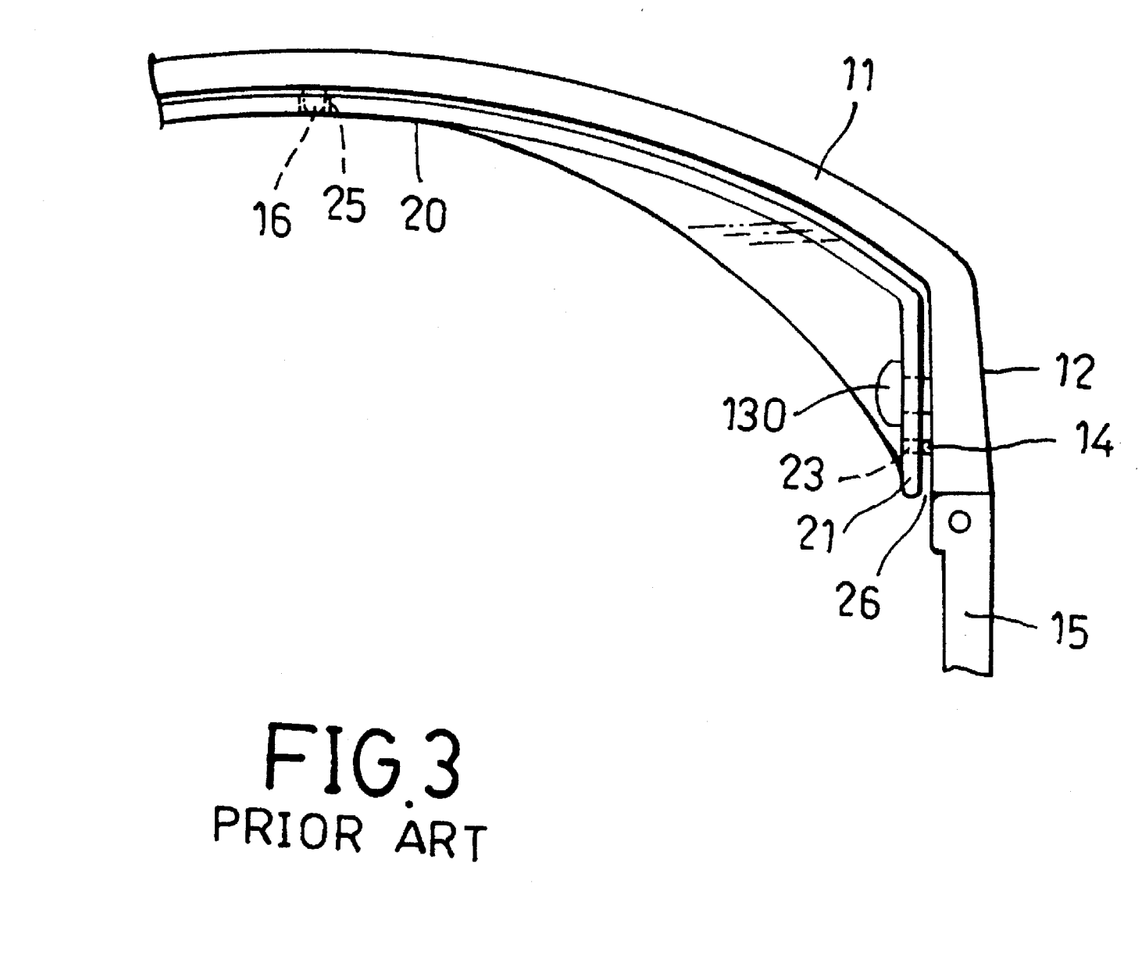
FIG. 3 is a top view of a portion of the conventional spectacles shown in FIG. 2.

Referring to FIGS. 2 and 3, the eye-protecting piece 2 is disposed vertically while the U-shaped frame member 1 is placed uprightly on two sides of the side plates 21 of the eye-protecting piece 2. Under this condition, the enlarged heads 130 can pass through the slots 22, and the U-shaped frame member 1 can be pivoted about the engaging rods 13 with respect to the transparent plate 20 such that the enlarged heads 130 are disposed across the width of the slots 22 while the bosses 14 extend selectively into one of the dents 23, thereby preventing the U-shaped frame member 1 from disengaging the eye-protecting piece 2. After the eye-protecting piece 2 and the U-shaped frame 1 have been connected, the slots 22 permit a slight movement of the engaging rods 13 therein. The intermediate portion 11 of the U-shaped frame member 1 is pushed towards the eye-protecting piece 2 so that the protuberance 16 engages in the through-hole 25 in the eye-protecting piece 1.

Note that in the above-mentioned conventional spectacles, the enlarged heads 130 of the engaging rods 13 can only prevent the eye-protecting piece 2 from disengaging the U-shaped frame member 1. The positioning of the eye-protecting piece 2 on the frame member 1 is performed by a combined action of the extension of the protuberance 16 in the through-hole 16, and the bosses 14 in one of the dents 23. Since the bending inward action of the side plate 21 relative to the transparent plate 20 is prevented by the enlarged heads 130 of the engaging lugs 13, a clearance 26 may formed between the side plates 21 of the eye-protecting piece 2 and the side portions 12 of the frame member 1 after a period of use. This consequently causes loose engagement between the bosses 14 and the dents 23 and eventually leads to poor angle adjustment between the eye-protecting piece 2 and the frame member 1.

SUMMARY OF THE INVENTION

Therefore, the main object of the present invention is to provide a pair of spectacles which has an eye-protecting piece that can be connected easily and securely to a frame member and that can be adjusted angularly relative to the frame member in an effective manner.

Accordingly, a pair of spectacles of the present invention comprises an eye-protecting piece which includes a transparent plate and a pair of side plates extending symmetrically from two opposed ends of the transparent plate, and a U-shaped frame member provided on an upper edge portion of the eye-protecting piece. The side plates of the eye-protecting piece respectively have an upper section with a top edge, an elongated notch extending downwardly from the top edge and a plurality of continuously-formed parallel ridges which project from an inner surface of the upper section and which define a plurality of parallel grooves that extend between the elongated notch and a free end portion of the side plate thereamong. The frame member has an elongated intermediate portion with two opposed ends and a protuberance which extends into an opening formed through an upper edge portion of the transparent plate, and two side portions which extend along the side plates from the opposed ends of the intermediate portion. Each of the side portions has an inner surface that is formed with a hollow rectangular sleeve. The sleeve is constituted by a first wall portion which extends perpendicularly from the side portion and which is located adjacent to a respective one of the ends of the intermediate portion, a second wall portion which is spaced farther away from the respective one of the ends of the intermediate portion than the first wall portion and which extends perpendicularly from the side portion, and a third wall portion which interconnects the first and second wall portions. The third wall portion has a resilient projection which extends toward the side portion. A portion of the upper section of the side plate between the notch and the free end portion thereof extends into the sleeve such that the first wall portion is received slidably in the notch, the second wall portion engages the free end portion of the side plate while the resilient projection engages one of the grooves.

Since the resilient projection of the frame member engages firmly one of the grooves of the eye-protecting piece after adjusting an angle between the frame member and the eye-protecting piece, the eye-protecting piece can be properly positioned relative to the frame member.

BRIEF DESCRIPTION OF THE DRAWINGS

Other features and advantages of the present invention will become more apparent in the following detailed description of the preferred embodiment with reference to the accompanying drawings, in which.

DETAILED DESCRIPTION OF THE PREFERRED EMBODIMENT

Figure 4:
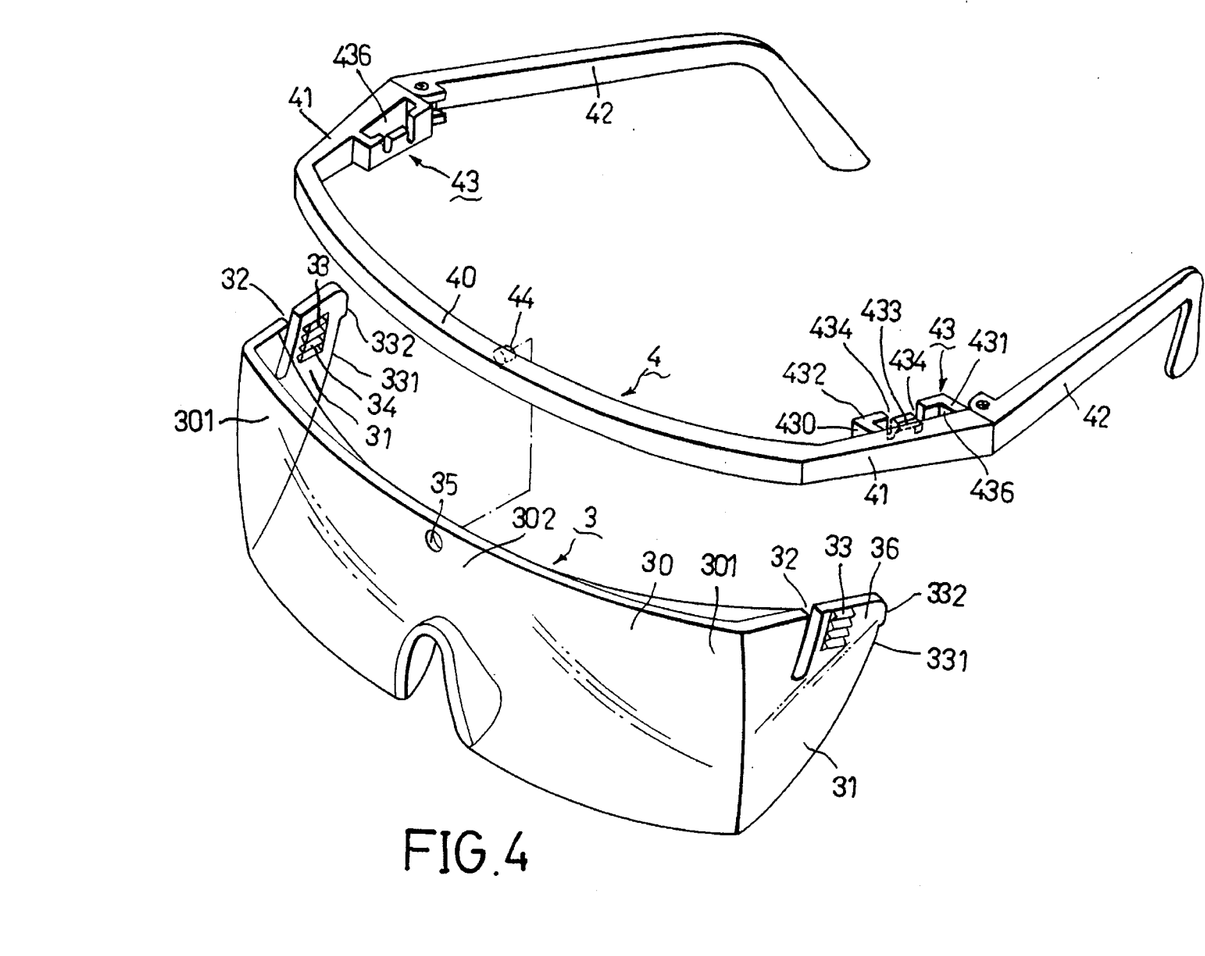
FIG. 4 shows an exploded view of a pair of spectacles according to the present invention.

Referring to FIG. 4, an exploded view of a pair of spectacles according to the present invention is shown to comprise an eye-protecting piece 3 and a U-shaped frame member 4 provided on an upper edge portion 302 of the eye-protecting piece 3.

The eye-protecting piece 3 includes an elongated transparent plate 30 to be disposed in front of the user's eyes. The transparent plate 30 has two opposed ends 301 and an upper edge portion 302 which is formed with an opening 35 and which extends between the opposed ends 301. The eye-protecting piece 3 further includes a pair of side plates 31 that extend symmetrically and integrally from the opposed ends 301 of the transparent plate 30. The side plates 31 are formed with two curved free end portions 331. Each of the side plates 31 has an upper section 36 with a top edge, an elongated notch 32 which extends downwardly from the top edge, and a plurality of continuously-formed parallel ridges 33 which project from an inner surface of the upper section 36 and which define a plurality of parallel grooves 34 that extend between the elongated notch 32 and a corresponding one of the free end portions 331.

The U-shaped frame member 4 has an elongated intermediate portion 40 with a protuberance 44 and two side portions 41 which extends from two opposed ends of the intermediate portion 40. A pair of legs 42 are hinged to free ends of the side portions 41. Each of the side portions 41 has an inner surface formed with a hollow rectangular sleeve 43 which confines a receiving space 436 therethrough. The sleeve 43 is constituted by a first wall portion 430 which extends perpendicularly from the side portion 41 and which is located adjacent to a respective one of the ends of the intermediate portion 40, a second wall portion 431 which is spaced farther away from the respective one of the ends of the intermediate portion 40 than the first wall portion 430 and which extends perpendicularly from the side portion 41, and a third wall portion 432 which interconnects the first and second wall portions 430, 431. The third wall portion 432 has an upper edge that is lower than that of the side portions 41, and a resilient projection 433 which extends from the upper edge of the same toward the side portion 41. The third wall portion 432 is further provided with a pair of notches 434 which extend downwardly from the upper edge thereof at two sides of the resilient projection 433 and which consequently provide more resiliency to the projection 433.

The free end portion 331 of each side plate 31 has a protrusion 332 and the second wall portion 431 of the sleeve 43 is provided with a tab 435 which extends towards the first wall portion 430.

Figure 5:
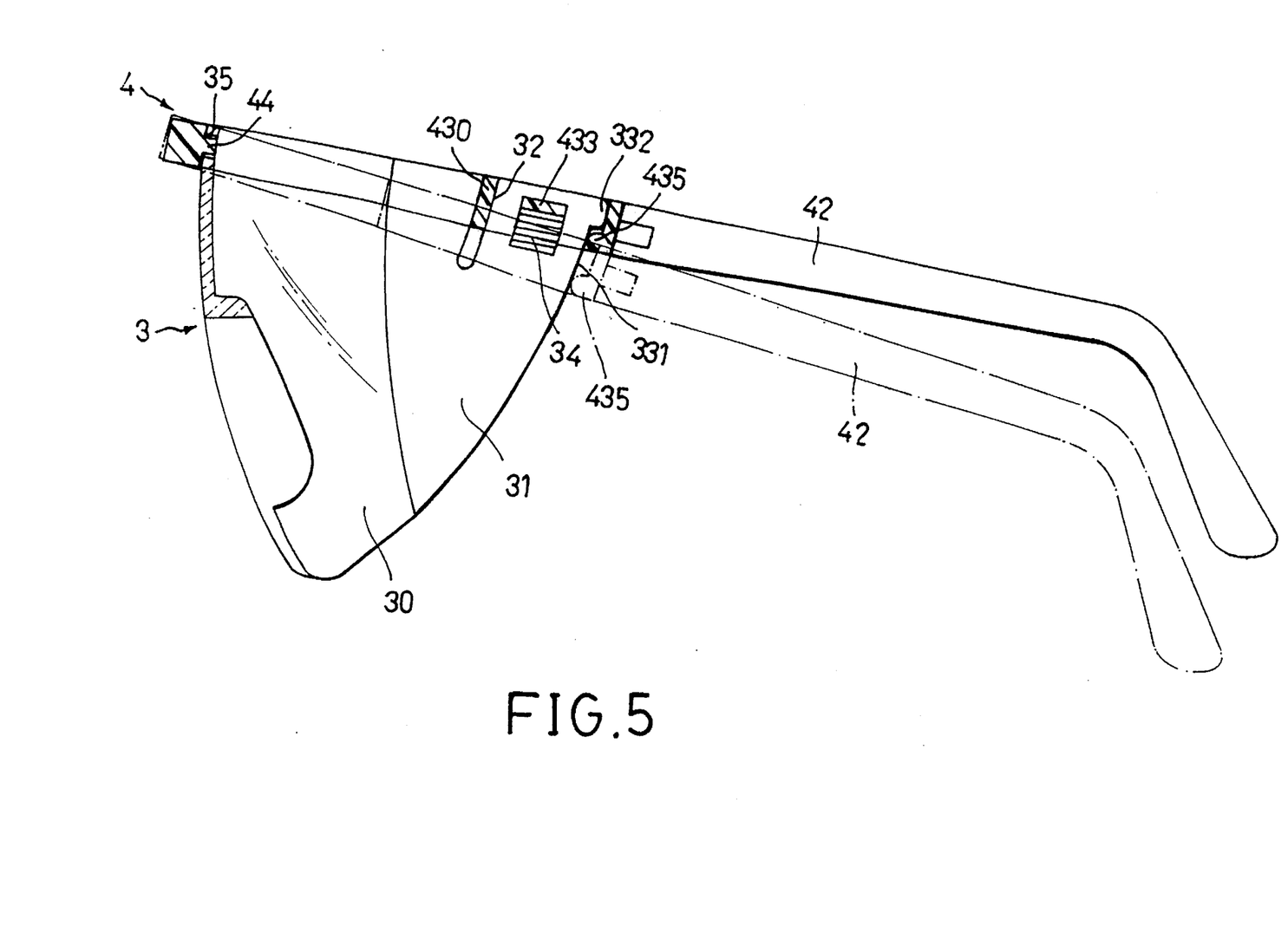
FIG. 5 shows a side view of the pair of spectacles according to the present invention, the perforated lines illustrating adjustment of a frame member of the spectacles relative an eye-protecting piece of the spectacles.
Figure 6:
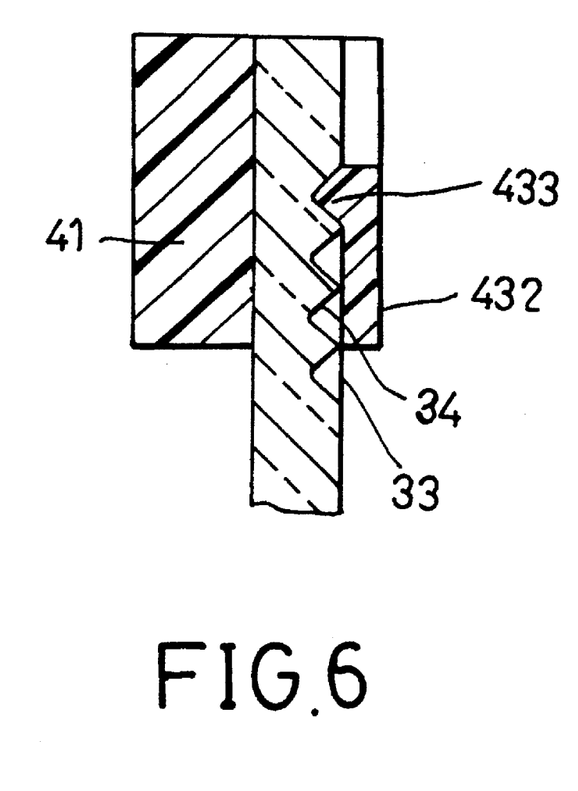
FIG. 6 illustrates how the frame member engaged the eye-protecting piece in accordance with the present invention.

Referring to FIG. 5, the U-shaped frame member 4 is disposed around the upper edge portion of the eye-protecting piece 3 with the protuberance 44 extending into the opening 35 of the transparent plate 30. The rectangular sleeve 43 can be sleeved over the upper section 36 of the side plate 31 by depressing the frame member 4 to pivot about the protuberance 44 such that a portion of the upper section 36 of a respective one of the side plates 31 between the notch 32 and the free end portion 331 extends into the space 436 confined by the sleeve 43. Under such a condition, the first wall portion 430 is received slidably in the notch 32, the second wall portion 431 engages the free end portion 331 of the side plate 31 and the resilient projection 433 engages one of the grooves 34, as shown in FIGS. 5 and 6. Note that the tab 435 of the second wall portion 431 slides past the protrusion 332 and is disposed underneath the latter so that untimely disengagement of the frame member 4 from the eye-protecting piece 3 does not occur.

When it is desired to adjust the frame member 4 relative to the eye-protecting piece 3, the frame member 4 can be further depressed as shown by the perforated lines in FIG. 5. Under this condition, even though the tab 4325 of the second wall portion 431 parts with the protrusion 332, the resilient projection 433 of the third wall portion 432 is moved abuttingly into another groove 34 so that the engagement between the eye-protecting piece 3 and the frame member 4 is not affected. An efficient angle adjustment between the eye-protecting piece 3 and the frame member 4 is thus provided.

With the invention thus explained it is obvious to those skilled in the art that various modifications and variations can be made without departing from the spirit and scope of the present invention. It is therefore intended that this invention be limited only as in the appended claims.

I claim:

1. A pair of spectacles comprising:

an eye-protecting piece including an elongated transparent plate to be disposed in front of a user's eyes, said transparent plate having two opposed ends and an upper edge portion extending between said opposed ends, said eye-protecting piece further including a pair of side plates extending symmetrically from said two opposed ends of said transparent plate, thereby forming two free end portions, each of said side plates having an upper section with a top edge, an elongated notch extending downwardly from said top edge and a plurality of continuously-formed parallel ridges projecting from an inner surface of said upper section and defining a plurality of parallel grooves that extend between said elongated notch and a corresponding one of said free end portions; and a U-shaped frame member provided on said upper edge portion of said transparent plate and on said top edges of said side plates, said frame member having an elongated intermediate portion with two opposed ends and a protuberance extending into an opening formed through said upper edge portion of said transparent plate, and two side portions extending along said side plates from said opposed ends of said intermediate portion, each of said side portions having an inner surface formed with a hollow rectangular sleeve constituted by a first wall portion extending perpendicularly from said side portion and located adjacent to a respective one of said ends of said intermediate portion, a second wall portion spaced farther away from said respective one of said ends of said intermediate portion than said first wall portion and extending perpendicularly from said side portion, and a third wall portion interconnecting said first and second wall portions, said third wall portion having a resilient projection extending toward said side portion, a portion of said upper section between said notch and said free end portion of said side plate extending into said rectangular sleeve such that said first wall portion is received slidably in said notch, said second wall portion engages said free end portion of said side plate and said resilient projection engages one of said grooves.

2. The spectacles as defined in claim 1, wherein said free end portion of said side plate has a protrusion extending therefrom, said second wall portion of said sleeve having a tab extending towards said first wall portion and capable of sliding over said protrusion so as to be located underneath of said protrusion, thereby preventing disengagement between said side plate and said frame member.

3. The spectacles as defined in claim 2, wherein said third wall portion has an upper edge and a pair of notches extending downwardly from said upper edge thereof at two sides of said resilient projection.

* * * * *

UNITED STATES PATENT AND TRADEMARK OFFICE
CERTIFICATE OF CORRECTION

PATENT NO. : 5,457,503
DATED : October 10, 1995
INVENTOR(S) : J. Chen

It is certified that error appears in the above-indentified patent and that said Letters Patent is hereby corrected as shown below:

| COLUMN | LINE | |
|---|---|---|
| 4 | 17 | "4325" should read --435-- |

Signed and Sealed this

Thirteenth Day of February, 1996

Attest:

BRUCE LEHMAN

Attesting Officer     Commissioner of Patents and Trademarks

REEXAMINATION CERTIFICATE (3251st)
United States Patent [19]
Chen

[11] B1 5,457,503
[45] Certificate Issued Jul. 1, 1997

[54] SPECTACLES WITH HIGH EFFICIENT ANGLE ADJUSTMENT

[76] Inventor: Jimmy Chen, 3F, No. 92, Ning-Po-Hsi St., Taipei, Taiwan

Reexamination Request:
No. 90/004,200, Apr. 1, 1996

Reexamination Certificate for:
Patent No.: 5,457,503
Issued: Oct. 10, 1995
Appl. No.: 352,347
Filed: Dec. 8, 1994

Certificate of Correction issued Feb. 13, 1996.

[51] Int. Cl.$^6$ ..................................................... G02C 1/04
[52] U.S. Cl. ........................... 351/105; 351/106; 351/120
[58] Field of Search ....................... 351/105, 106, 351/107, 108, 109, 111, 115, 121, 47, 57, 59, 103, 104, 41, 120, 83, 86; 2/450, 451, 452

[56] References Cited

U.S. PATENT DOCUMENTS 1,380,166   5/1921   Wall et al. .
2,427,469   9/1947   Morley et al. .
5,357,292   10/1994  Wiedner ................................. 351/105

OTHER PUBLICATIONS

Catalog: Uvex sportstyle #83, Uvex Winter Optical, Inc., Smithfield, RI, 1990.

Catalog: Uvex star-flex 9192, Uvex Winter Optik Gmbh, Fürth, Germany, May 1993.

*Primary Examiner*—Hung Xuan Dang

[57] ABSTRACT

The pair of spectacles includes an eye-protecting piece with a transparent plate and two side plates, and a U-shaped frame member. Each of the side plates has an upper section with a top edge, an elongated notch extending downwardly from the top edge, and a plurality of parallel ridges projecting from an inner surface and defining a plurality of parallel grooves which extend between the notch and a free end portion thereof. The frame member has an elongated intermediate portion with two side portions. Each of the side portions has an inner surface formed with a hollow rectangular sleeve constituted by a first wall portion which extends perpendicularly from the side portion, a second wall portion spaced farther away from the intermediate portion than the first wall portion and extending perpendicularly from the side portion, and a third wall portion interconnecting the first and second wall portions. The third wall portion has a resilient projection extending toward the side portion. After assembly, a portion of the side plate between the notch and the free end portion thereof extends into the sleeve such that the first wall portion is received slidably in the notch, the second wall portion engages the free end portion of the side plate while the resilient projection engages one of the grooves.

// B1 5,457,503

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–2 and 3 are cancelled.

* * * * *